US006451337B1

(12) United States Patent
Smith et al.

(10) Patent No.: US 6,451,337 B1
(45) Date of Patent: *Sep. 17, 2002

(54) CHITOSAN-BASED NITRIC OXIDE DONOR COMPOSITIONS

(75) Inventors: Daniel J. Smith, Stow, OH (US); Sibel Yazici, Karamursel-Izmit (TR)

(73) Assignee: The University of Akron, Akron, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/576,096

(22) Filed: May 22, 2000

Related U.S. Application Data

(63) Continuation-in-part of application No. 09/199,732, filed on Nov. 25, 1998, now Pat. No. 6,261,594.

(51) Int. Cl.[7] .......................... A61L 15/00; A61F 13/00; A61K 9/00; C08B 37/08
(52) U.S. Cl. ...................... 424/445; 424/422; 424/443; 424/449; 424/400; 424/451; 424/489; 424/464; 424/45; 536/20
(58) Field of Search ................................ 424/400, 451, 424/489, 464, 45, 422, 443, 449; 536/20; 31/722

(56) References Cited

U.S. PATENT DOCUMENTS

| 3,163,094 A | 12/1964 | Reilly | 260/576 |
| 3,826,832 A | 7/1974 | Anderson | 424/250 |

(List continued on next page.)

FOREIGN PATENT DOCUMENTS

| DE | 2126035 | 12/1971 |
| DE | 211789 | 8/1982 |
| DE | 211789 | * 7/1984 |
| EP | 425154 B1 | 9/1993 |
| WO | WO 89/12627 | 12/1989 |
| WO | WO 90/09785 | 9/1990 |
| WO | WO 91/04022 | 4/1991 |
| WO | WO 91/05551 | 5/1991 |
| WO | WO 92/05149 | 4/1992 |
| WO | WO 93/07114 | 4/1993 |
| WO | WO 93/20088 | 10/1993 |
| WO | WO 93/20806 | 10/1993 |
| WO | WO 95/10267 | 4/1995 |
| WO | WO 96/13164 | 5/1996 |

OTHER PUBLICATIONS

Ignarro et al. *J. Pharmacol. Exp. Ther.* v. 218, pp. 739–749, 1981.

Tokura et al. "Physicochemical, Biomedical and Biological Properties of Chitin Derivatives", *Chitin, Chitosan and Related Enzymes* pp. 303–309, (Academic Press, 1984).

(List continued on next page.)

*Primary Examiner*—Thurman K. Page
*Assistant Examiner*—Isis Ghali
(74) *Attorney, Agent, or Firm*—Renner, Kenner, Greive, Bobak, Taylor & Weber

(57) ABSTRACT

A chitosan-based polymeric nitric oxide donor composition comprising a modified chitosan polymer and a nitric oxide [$N_2O_2$] dimer, wherein the nitric oxide [$N_2O_2$] dimer is bonded directly to the backbone of the modified chitosan polymer without further binding through a nucleophile residue or moiety. The chitosan-based polymeric nitric oxide donor composition is capable of site specific delivery and controlled release of nitric oxide under physiological conditions. The chitosan-based polymeric nitric oxide donor composition further provides a carrier having medically beneficial properties. A method is further included for preparing a chitosan-based polymeric nitric oxide donor composition comprising reacting a nitric oxide dimer (80–100 p.s.i.) with a modified chitosan polymer in the presence of sodium methoxide at room temperature. The chitosan-based polymeric nitric oxide composition can be incorporated into dry powder inhalers, wound dressings, implants, injectables, condoms, wound dressings and prosthesis coatings for use in a variety of medical applications in which an effective dosage of nitric oxide is indicated as a preferred method of treatment.

28 Claims, 3 Drawing Sheets

$R=$ —$CHCH_3CH_2CH_2COO^-Na^+$
—$CH_2CH_2COO^-Na^+$
—$CH_2CH_2COOCH_3$
—$CH_2COO^-Na^+$
—$CH_2CH_2CH_3$

U.S. PATENT DOCUMENTS

| | | | | |
|---|---|---|---|---|
| 4,265,714 | A | 5/1981 | Nolan et al. | 204/1 |
| 4,482,533 | A | 11/1984 | Keith | 421/28 |
| 4,638,079 | A | 1/1987 | Inskip | 560/4 |
| 4,708,854 | A | 11/1987 | Grinstead | 423/235 |
| 4,835,265 | A | 5/1989 | Muzzarelli | 536/18.7 |
| 4,921,683 | A | 5/1990 | Bedell | 423/235 |
| 4,952,289 | A | 8/1990 | Ciccone et al. | 204/129 |
| 4,954,526 | A | 9/1990 | Keefer | 514/611 |
| 4,985,471 | A | 1/1991 | Ohta et al. | 522/27 |
| 5,039,705 | A | 8/1991 | Keefer et al. | 514/611 |
| 5,087,631 | A | 2/1992 | Shaffer et al. | 514/342 |
| 5,087,671 | A | 2/1992 | Loeppky et al. | 525/328.2 |
| 5,094,815 | A | 3/1992 | Conboy et al. | 422/52 |
| 5,155,137 | A | 10/1992 | Keefer et al. | 514/611 |
| 5,208,233 | A | 5/1993 | Keefer et al. | 514/231.8 |
| 5,212,204 | A | 5/1993 | Keefer et al. | 514/647 |
| 5,234,956 | A | 8/1993 | Lipton | 514/724 |
| 5,250,550 | A | 10/1993 | Keefer et al. | 514/357 |
| 5,366,997 | A | 11/1994 | Keefer et al. | 514/611 |
| 5,389,675 | A | 2/1995 | Christodoulou et al. | 514/492 |
| 5,405,919 | A | 4/1995 | Keefer et al. | 525/377 |
| 5,482,925 | A | 1/1996 | Hutsell | 514/11 |
| 5,691,423 | A | 11/1997 | Smith et al. | 525/377 |
| 6,261,594 | B1 * | 7/2001 | Smith et al. | |

OTHER PUBLICATIONS

Ignarro et al. *Annu. Rev. Pharmacol. Toxicol.* v. 25, pp. 171–191, 1985.

Kruszyna et al. *Toxicol. Appl. Parmacol.* v. 91, pp. 429–438, 1987.

Kuhn, et al. *Cardiovasc. Pharmacol.* v. 14 (Suppl. 11), pp. S47–S54, 1989.

Ignarro. *Annu. Rev. Pharmacol. Toxicol.* v. 30, pp. 535–560, 1990.

Muzzarelli, R. et al. "Antimicrobial Properties of N–carboxybutyl Chitosan." *Antimicrobial Agents and Chemotherapy* v. 34 (10), pp. 2019–2023, Oct. 1990.

Wilcox et al. *Chem. Res. Toxicol.* v. 3, pp. 71–76, 1990.

Biagini, Graziella et al. "Morphological Study of the Capsular Organization Around Tissue Expanders Coated with N–carboxybutyl Chitosan", *Biomaterials* v. 12, pp. 287–291, Apr. 1991.

Biagini, Graziella et al. "Wound Management with N–carboxybutyl Chitosan", *Biomaterials* v. 12, pp. 281–286, 1991.

Muzzarelli, R., Weckx, M. and Bicchiega, V. "N–carboxybutyl Chitosan as a Wound Dressing and a Cosmetic Ingredient". *Chim. Oggi.* v. 9 (4), pp. 33–37, 1991.

Smith et al. "A Potpourri of Biologically Reactive Intermediates in Biological Reactive Intermediates IV. Molecular and Cellular Effects and Their Impact on Human Health". (Witmer et al., eds.), *Advance in Experimental Medicine and Biology* v.283, pp. 365–369, (Plenum Press: New York, 1991).

\* cited by examiner

CHITOSAN-BASED NITRIC OXIDE DONOR COMPOSITIONS

CROSS REFERENCE TO RELATED APPLICATIONS

This application is a continuation-in-part of U.S. Ser. No. 09/199,732, filed Nov. 25, 1998. Now U.S. Pat. No. 6,261,594.

TECHNICAL FIELD OF THE INVENTION

The present invention is directed to a polymeric composition that is capable of releasing nitric oxide (NO). The present invention is more particularly directed to a chitosan-based polymeric nitric oxide donor composition comprising a modified chitosan polymer and a nitric oxide $[N_2O_2]^-$ dimer, which provides site specific delivery and controlled release of nitric oxide under physiological conditions; pharmacological compositions comprising the polymeric composition; and the use of the polymeric composition to treat biological disorders for which an effective dosage of exogenous nitric oxide is indicated as a preferred method of treatment.

BACKGROUND OF THE INVENTION

The chemical versatility of the nitric oxide (NO) molecule allows it to participate in a variety of physiologic processes. Nitric oxide (NO) reacts in biological systems with molecular oxygen ($O_2$), superoxide ($O_2^-$) and transition metals to form high nitrogen oxides ($NO_x$), peroxynitrite ($OONO^-$) and metal-nitrosyl adducts which have various toxicities and biological activities.

The role of the nitric oxide (NO) molecule has been implicated in many physiologic processes, such as regulation of pulmonary hypertension via endothelium derived relaxing factor (EDRF)-induced vascular relaxation, central and peripheral neurotransmission, modulation of intestinal motility, regulation of male erectile function, macrophage-induced cytostasis and cytotoxicity, platelet inhibition, and non specific immune response.

Nitric oxide synthases (NOS) catalyze the oxidation of the substrate L-arginine into L-citrulline and nitric oxide (NO) in a variety of mammalian cell populations, such as pulmonary mucosa, submucosa, muscle, nerve and endothelium, reflecting the diverse biological activities of nitric oxide (NO).

Investigations have been conducted which pharmacologically manipulate the tissue level of nitric oxide (NO) by exogenous delivery of nitric oxide (NO) through inhalation of nitric oxide (NO) gas into the lungs via an endotracheal tube during mechanical ventilation. Although inhalation of nitric oxide gas has been useful in the treatment of such conditions as pulmonary hypertension, there are several disadvantages and limitations with this particular mode of therapy. Nitric oxide (NO) inhalation therapy requires large gas tanks, expensive monitoring equipment, and a highly trained and skilled technician to operate the tanks and equipment, to deliver a therapeutically effective amount of nitric oxide (NO) gas to a patient. Due to the volatility, hazardous and poisonous properties of nitric oxide (NO) gas, safe delivery of exogenous nitric oxide (NO) has been difficult to achieve.

In response to the great need in the art of nitric oxide (NO) therapy to develop a more convenient, less expensive and safer method to deliver exogenous nitric oxide (NO) to patients, numerous donor compounds have been developed to administer an effective dosage of exogenous nitric oxide (NO) in biological systems under physiological conditions.

A number of compounds have been developed which are capable of binding, delivering and releasing nitric oxide (NO) in physiological conditions upon being metabolized, including nitrovasodilators such as glyceryl trinitrite and sodium nitroprusside. (Ignarro et al., *J. Pharmacol. Exp. Ther.*, 218, 739–749 (1981); Ignarro, *Annu. Rev. Pharmacol. Toxicol.*, 30, 535–560 (1990); Kruszyna et al., *Toxicol. Appl. Pharmacol.*, 91, 429–438 (1987); Wilcox et al., *Chem. Res. Toxicol.*, 3, 71–76 (1990)). Although compounds such as glyceryl trinitrite and sodium nitroprusside are relatively stable under physiological conditions, a tolerance to glyceryl trinitrite via the exhaustion of the relevant enzyme/cofactor system is sometimes experienced in some applications, thus its use as a nitric oxide donor is limited. (Ignarro et al., *Annu. Rev. Pharmacol. Toxicol.*, 25, 171–191 (1985); Kuhn et al., *J. Cardiovasc. Pharmaol.*, 14 (Suppl. 11), S47–S54 (1989)). Furthermore, toxicity can develop from prolonged administration of sodium nitroprusside due to the metabolic production of cyanide. (Smith et al., "A Potpourri of Biologically Reactive Intermediates" in *Biological Reactive Intermediates IV. Molecular and Cellular Effects and Their Impact on Human Health* (Witmer et al., eds.), Advances in Experimental Medicine and Biology Volume 283 (Plenum Press: New York, 1991), pp. 365–369).

A number of biodegradable compounds, such as primary, secondary, and polyamines, have been developed which are capable of delivering nitric oxide (NO), and releasing nitric oxide (NO) in physiologic conditions upon being metabolized. Keefer et al, U.S. Pat. No. 4,954,526 disclose a method of treating cardiovascular disorders with an effective amount of a stabilized complex formed from nitric oxide and primary amines and esters, ethers, of the formula [R—N(H)N(NO)—]$_y$X.

Further compounds have been developed that comprise diazenium diolates (NONOates) bound to polymers. NONOates are complexes of nitric oxide (NO) and nucleophiles ($X^-$) in which a nitric oxide (NO) dimer is bound to the nucleophilic residue via a nitrogen atom, thus forming a NONOate having the following chemical formula:

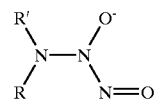

Wherein R and R' are the same or different, and constitute any of a number of known organic moieties.

Traditionally, the synthesis of NONOates was accomplished by dissolving a nucleophile in an organic solvent and exposing the solution to a few atmospheres of NO gas for a period of a few days. A nucleophile, as the term is used above, is defined as an ion or molecule that donates a pair of electrons to an atomic nucleus to form a covalent bond. (*Hawley's Condensed Chemical Dictionary, Twelfth Edition*). Useful nucleophiles for the synthesis of NONOates have traditionally included primary, secondary or polyamines. When a polyamine, such as spermine is used as the nucleophile, zwitterions are formed. Upon exposure of the nucleophile solution to NO gas, the NO dimer behaves as an electron pair acceptor, thus forming a covalent bond with the electron pair-donating nucleophile. This reaction results in a nitric oxide/nucleophile complex. The nucleophile moiety of the nitric oxide/nucleophile adduct can be further be bound to a polymer, such as a polysaccharide, such that the nucleophile moiety of the nitric oxide/ nucleophile complex forms part of the polymer itself. NONOates are useful as nitric oxide donors in biological systems due to their ability to spontaneously disassociate under physiological conditions to regenerate the free nucleophile and molecular nitric oxide (NO).

Keefer et al, U.S. Pat. Nos. 5,250,550 and 5,155,137 disclose complexes of nitric oxide (NO) and polyamines, such as spermine and spermadine, useful in treating cardiovascular disorders, such as pulmonary hypertension, and which release nitric oxide (NO) under physiological conditions in a sustained and controlled manner. These complexes are made into pharmaceutical compositions by combination with medically acceptable carriers or diluents. Specifically, these compounds can be prepared into injectables by dissolving, suspending or emulsifying them in an aqueous or non-aqueous solvent.

Keefer et al, U.S. Pat. No. 5,212,204 discloses a method for lowering blood pressure using an antihypertensive composition comprising the $N_2O_2^-$ functional group, an inorganic or organic moiety and a pharmaceutically acceptable cation. The organic or inorganic moiety is any moiety that will form the anithypertensive composition and release nitric oxide (NO) under physiological conditions upon decomposition.

Keefer et al, U.S. Pat. Nos. 5,208,233 and 5,039,705 disclose a method of treating cardiovascular disorders that will respond to a decrease in blood pressure, such as chronic hypertension, acute congestive heart failure, angina, acute myocardial infarction, left ventricular failure, cerebrovascular insufficiency and intracranial hemorrhage, by using an antihypertensive composition of secondary amines and nitric oxide adducts.

Keefer et al, U.S. Pat. No. 5,366,997 disclose a cardiovascularly active composition possessing antihypertensive properties comprising oxygen substituted derivatives of nucleophile-nitric oxide adducts as nitric oxide donor prodrugs.

Christodoulou et al, U.S. Pat. No. 5,389,675 disclose mixed ligand metal complexes of nitric oxide-nucleophile adducts which are capable of releasing nitric oxide (NO), and are useful as cardiovascular agents. The nitric oxide-nucleophile complex ligand are coordinated via the oxygen donor atoms of the bidentate $N_2O_2^-$ functionality to metal centers, which are further bound to one or more additional ligands.

Smith et al, U.S. Pat. No. 5,691,423 disclose a polymeric composition capable of releasing nitric oxide (NO) in which the nitric oxide releasing functional group $[N_2O_2]^-$ is bound to the polysaccharide via a nucleophile moiety or residue.

Many of the nitric oxide-nucleophile (NONOates) complexes have been promising as pharmacological compounds because, unlike, nitrovasodialators such as glyceryl trinitrite and sodium nitroprusside, they spontaneously release nitric oxide (NO) in aqueous solutions under physiological conditions without first having to be metabolized.

Although the NONOate complexes release molecular nitric oxide (NO) without first having to be metabolized, pharmacological applications have been limited by their propensity to distribute evenly throughout a given medium and their spontaneous release of nitric oxide (NO) in aqueous media, thus compromising site specific delivery of nitric oxide (NO) to target tissues.

Accordingly, there remains a great need to develop a low cost, readily biodegradable, biocompatible nitric oxide donor polymer composition comprising a nitric oxide $[N_2O_2]^-$ dimer and a medically beneficial carrier molecule, capable of improved site specific delivery and controlled release of nitric oxide (NO) to target tissues under physiological conditions, without the further side effects of the nitric oxide donor compounds disclosed in the prior art.

SUMMARY OF THE INVENTION

It is an object of the present invention to provide a chitosan-based polymeric nitric oxide donor composition comprising a modified chitosan polymer and a nitric oxide $[N_2O_2]^-$ dimer.

It is a further object of the present invention to provide chitosan-based polymeric nitric oxide donor compositions in which the nitric oxide $[N_2O_2]^-$ dimer is bound directly to the modified chitosan polymer.

It is a further object of the present invention to provide a chitosan-based polymeric nitric oxide donor composition which further includes a medically beneficial carrier molecule.

It is a further object of the present invention to provide a chitosan-based polymeric nitric oxide donor composition capable of site specific delivery and controlled release of nitric oxide under physiological conditions.

It is a further object of the present invention to provide chitosan-based polymeric nitric oxide donor compositions having first order nitric oxide release kinetics.

It is a further object of the present invention to provide a method of preparing a chitosan-based polymeric nitric oxide donor composition comprising reacting a nitric oxide (NO) dimer with a modified chitosan polymer.

It is a further object of the present invention to provide a chitosan-based polymeric composition to treat respiratory distress, emphysema, external wounds, internal wounds and for coating vascular grafts.

These and other objects of the present invention, together with the advantages over the prior art relating to nitric oxide donor compositions, which should be become apparent from the specification which follows, are accomplished by the composition and method which is hereafter described and claimed.

The present invention, therefore, provides a chitosan-based polymeric nitric oxide donor composition comprising a modified chitosan polymer and a nitric oxide $[N_2O_2]^-$ dimer, in which the nitric oxide $[N_2O_2]^-$ dimer is bound directly to a nitrogen atom in the backbone of the modified chitosan polymer. The chitosan-based nitric oxide donor composition of the present invention further comprises a medically beneficial carrier molecule. The chitosan-based nitric oxide donor composition has first order nitric oxide release kinetics and provides site specific delivery and controlled release of nitric oxide under physiological conditions.

The nitric oxide donor composition of the present invention comprises a chitosan polymer and a nitric oxide $[N_2O_2^-]$ dimer, said composition having the general formula:

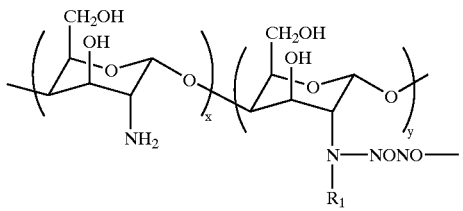

wherein $R_1$ is an organic group having from 1 to about 18 carbon atoms;

wherein x is from about 0.5 to about 0.8;

wherein y is from about 0.2 to about 0.5; and wherein x and y are the mole fractions of each unit and the sum of x and y is 1.

The present invention further provides a method for preparing a nitric oxide donor composition comprising reacting a nitric oxide $[N_2O_2]^-$ dimer with a chitosan polymer, said chitosan polymer having the following general formula:

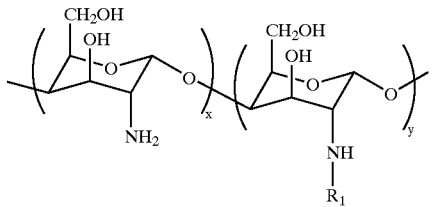

wherein $R_1$ is an organic group having from 1 to about 18 carbon atoms;

wherein x is from about 0.5 to about 0.8;

wherein y is from about 0.2 to about 0.5; and wherein x and y are the mole fractions of each unit and the sum of x and y is 1.

In one preferred embodiment, the present invention further provides a method for the preparing a nitric oxide donor composition comprising reacting nitric oxide (80–100 p.s.i.) with a chitosan polymer in the presence of sodium methoxide at room temperature, said chitosan polymer having the following general formula:

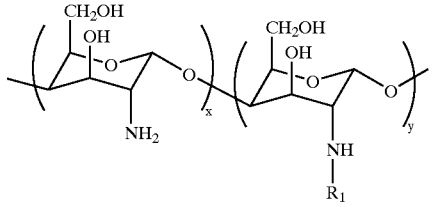

wherein $R_1$ is an organic group having from 1 to about 18 carbon atoms;

wherein x is from about 0.5 to about 0.8;

wherein y is from about 0.2 to about 0.5; and wherein x and y are the mole fractions of each unit and the sum of x and y is 1.

DETAILED DESCRIPTION OF THE INVENTION

Figure 1:
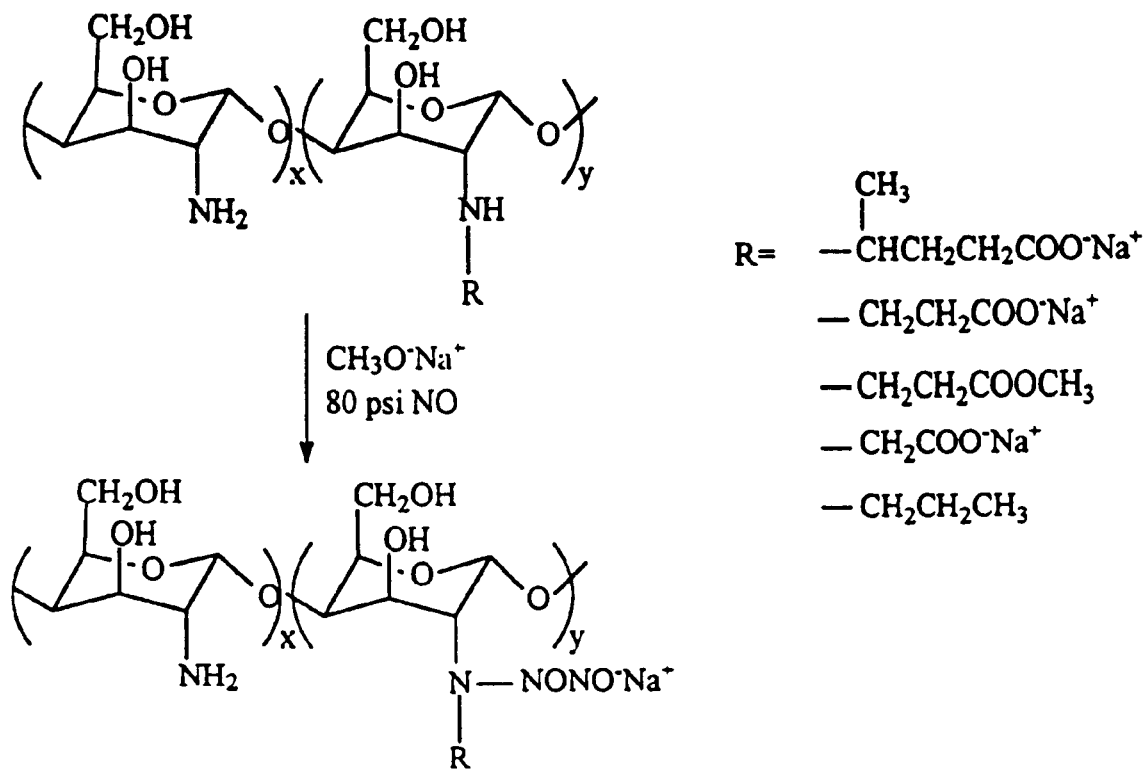
FIG. 1 is a schematic representation of the mechanism of synthesis and chemical structures of the chitosan-based nitric oxide donor composition of the present invention.

The present invention provides a chitosan-based polymeric composition capable of site specific delivery and controlled release of nitric oxide to target tissues comprising a modified chitosan polymer and a nitric oxide $[N_2O_2]^-$ dimer. The nitric oxide (NO) dimer is bound or "loaded" onto the modified chitosan polymer. Thus, the modified chitosan polymer acts as a carrier of the nitric oxide (NO) dimer. The nitric oxide $[N_2O_2]^-$ dimer is covalently bound to the modified chitosan polymer, forming a diazenium diolate (NONOate) derivative of the modified chitosan polymer. Chemical bonding of the nitric oxide $[N_2O_2]^-$ dimer to the modified chitosan polymer is achieved by covalent bonding of the nitric oxide $[N_2O_2]^-$ dimer directly to a nitrogen atom in the backbone of the modified chitosan polymer, such that the nitric oxide $[N_2O_2]^-$ dimer becomes incorporated, or part of the modified chitosan polymer. The terminology modified chitosan polymer, as used throughout the specification, is defined as any biologically compatible derivative of chitosan.

It is known in the prior art to bond a nitric oxide-releasing $[N_2O_2]^-$ functional group or dimer to a polymer, such as a polysaccharide, via a nucleophile moiety. In this situation, the nitric oxide (NO) dimer is bound to a nucleophile moiety forming a nitric oxide/nucleophile complex. The nitric oxide/nucleophile complex is subsequently chemically or physically bound to a polymer, such that the nitric oxide/nucleophile complex is associated with, becomes part of, incorporated with or contained within the polymer matrix.

It has been discovered that a nitric oxide $[N_2O_2]^-$ dimer can be covalently bonded to a nucleophilic nitrogen atom on the modified chitosan polymer, without first having to be bonded to a nuclephilic moiety as described in the prior art. Specifically, the modified chitosan polymer is synthesized such that the primary amine in the modified chitosan polymer is converted into a secondary amine which serves as the nucleophilic reaction site for the binding of the nitric oxide-releasing $[N_2O_2]^-$ dimer.

The nitric oxide donor composition of the present invention comprises a chitosan polymer and a nitric oxide $[N_2O_2^-]$ dimer, said composition having the general formula:

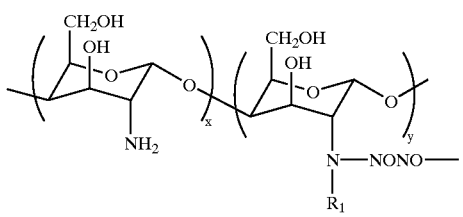

wherein $R_1$ is an organic group having from about 1 to about 18 carbon atoms, x is from about 0.5 to about 0.8, y is from about 0.2 to about 0.5 and x and y are the mole fractions of each unit and the sum of x and y is 1.

Preferably, the organic group, $R_1$, is an alkyl group having about 1 to about 18 carbon atoms. The organic group may by straight or branch chained. The organic group may also contain heteroatoms, such as nitrogen, oxygen, sulfur and phosphorous. The organic group, $R_1$, may contain an ester functionality, and may be represented by the following formula:

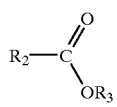

wherein $R_2$ is an organic group having from about 1 to about 18 carbon atoms. $R_2$ may by straight or branch chained. $R_2$ may also contain heteroatoms, such as nitrogen, oxygen, sulfur and phosphorous; and wherein $R_3$ is methyl. Preferably, $R_2$ is an alkyl group having from about 1 to about 18 carbon atoms.

The organic group, $R_1$, may alternatively contain an acid functionality, and may be represented by the following formula:

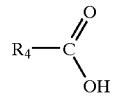

wherein $R_4$ is an organic group having from about 1 to about 18 carbon atoms. $R_4$ may by straight or branch chained. $R_4$ may also contain heteroatoms, such as nitrogen, oxygen, sulfur and phosphorous. Preferably, $R_4$ is an alkyl group having from about 1 to about 18 carbon atoms.

In one embodiment, the polymeric nitric oxide donor composition may also comprise a metal cation, $M^+$, bonded to an oxygen atom on the nitric oxide dimer, to stabilize the charge on the polymer. In this embodiment, the polymeric nitric oxide donor may be represented by the following general formula:

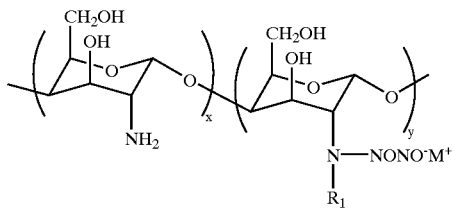

Without limitation, the metal cation, $M^+$, may be selected from cations of alkali metals. Preferably, the metal cation is $Na^+$.

Alternatively, the polymeric nitric oxide donor composition may contain positive charge on amine functionality of the chitosan polymer to stabilize the charge on the polymer. In this embodiment, the polymeric nitric oxide donor may be represented by the following general formula:

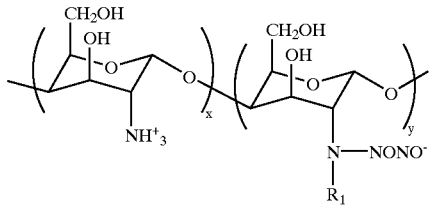

The present invention provides a chitosan-based NON-Oate composition wherein the composition further comprises a medically beneficial carrier. It is known that modified chitosan polymers, such as N-carboxybutyl chitosan, possess medically beneficial properties. For example, wound dressings incorporating N-carboxybutyl chitosan stimulate ordered regeneration and vascularization of tissue and allow for gas exchange, resulting in a reduction of secondary infections and scar formation. (Muzzarelli, R. et al., "N-carboxybutyl Chitosan as a Wound Dressing and a Cosmetic Ingredient", *Chim. Oggi.* Vol 9, No. 4, 33–37 (1991); Biagini, Graziella et al. "Wound Management with N-carboxybutyl Chitosan", *Biomaterials*, Vol. 12, 281–286 (1991); Biagini, Graziella et al. "Morphological Study of the Capsular Organization Around Tissue Expanders Coated with N-carboxybutyl Chitosan", *Biomaterials*, Vol. 12, 287–291 (1991). It is also known that N-carboxybutyl chitosan possesses significant antibacterial properties against candidae, staphylococci, streptococci and enterococci. (Muzzarelli, R. et al. "Antimicrobial Properties of N-carboxybutyl Chitosan." *Antimicrobial Agents and Chemotherapy*, 2019–2023 (1990).

By way of exemplification, but not in limitation, suitable modified chitosan polymers include N-carboxymethyl chitosan (N—CMC), N-carboxyethyl chitosan (N—CEC), the methyl ester of N-carboxyethyl chitosan (N—CEC—Me ester), N-carboxybutyl chitosan (N—CBC), N-propyl chitosan (N—PC), and the like. The modified chitosan polymers employed in the present invention have the following general chemical formula:

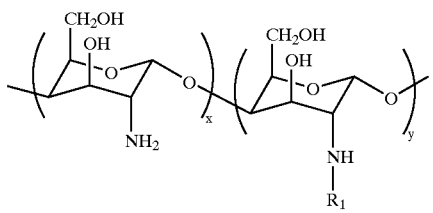

wherein $R_1$ is an organic group having from 1 to about 18 carbon atoms. $R_1$ may also contain heteroatoms, such as nitrogen, oxygen, sulfur and phosphorous. $R_1$ may also contain ester or acid functionalities. Preferably, the organic group, $R_1$, is a straight or branched chain alkyl group having from about 1 to about 18 carbon atoms;

x is from about 0.5 to about 0.8;

y is from about 0.2 to about 0.5; and wherein x and y represent the mole fraction of each unit and the sum of x and y is 1.

More preferably, the organic group, $R_1$, is selected from $CH_3CHCH_2CH_2COO^-$, $CH_2CH_2COO^-$, $CH_2CH_2COOCH_3$, $CH_2COO^-$ and $CH_2CH_2CH_3$.

Synthesis of N-Carboxybutyl Chitosan (N—CBC) and N-Carboxymethyl Chitosan (N—CMC)

The modified chitosan polymers, N-carboxybutyl chitosan (N—CBC) and N-carboxymethyl chitosan (N—CMC), employed in the present invention were synthesized by the method of Muzzarelli, U.S. Pat. No. 4,835,265, incorporated herein by reference. N-carboxybutyl chitosan (N—CBC) has the following chemical formula:

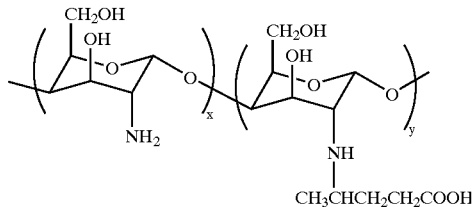

and N-carboxymethyl chitosan (N—CMC) has the following chemical formula:

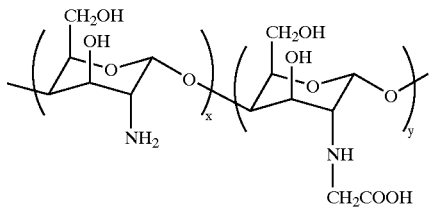

wherein:
x is from about 0.5 to about 0.8;
y is from about 0.2 to about 0.5; and
wherein x and y represent the mole fraction of each unit and the sum of x and y is 1.

Briefly, 3.6 grams of chitosan was dissolved in 80 milliliters of $H_2O$, containing 50% weight percent levulinic acid and glyoxilic acid (1.5 times the molar amount of chitosan). The addition of levulinic acid and glyoxilic acid to the chitosan results in the formation of a Schiff's base. Twelve hours after the reduction of the Schiff's bases, the pH of the was adjusted to 7.0 with 0.1M NaOH. N-carboxybutyl chitosan (N—CBC) was subsequently dialyzed against distilled $H_2O$ for three days and freeze dried to obtain a soft spongy product having a percent yield of 58 percent. N-carboxymethyl chitosan precipitated at 7.0, and was filtered off and washed in an ethanol solution. The N-carboxymethyl chitosan (N—CMC) was freeze dried and had a percent yield of 87 percent.

Synthesis of N-Carboxyethyl Chitosan (N—CEC) and the Methyl Ester of N-Carboxyethyl Chitosan (N—CEC—Me Ester)

N-carboxyethyl chitosan (N—CEC) and the methyl ester of N-carboxyethyl chitosan (N—CEC—Me ester) were synthesized by the method of Bartowiak et al, incorporated herein by reference. N-carboxyethyl chitosan (N—CEC) has the following chemical formula:

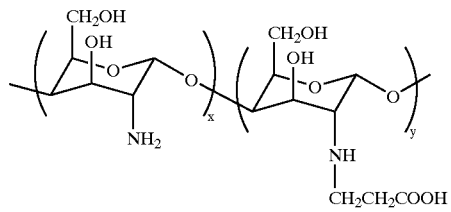

and the methyl ester of N-carboxyethyl chitosan (N—CEC—Me ester) has the following formula:

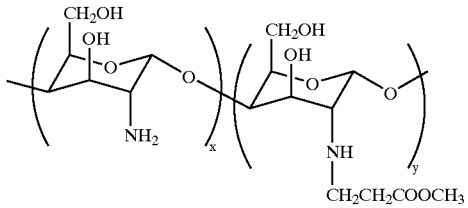

wherein:
x is from about 0.5 to about 0.8;
y is from about 0.2 to about 0.5; and
wherein x and y represent the mole fraction of each unit and the sum of x and y is 1.

Briefly, 2.0 grams of chitosan dissolved in 100 milliliters of 0.1 molar acetic acid was reacted with 4.5 milliliters of methyl acrylate (5 times the molar amount of chitosan) in 70 milliliters of methanol (MeOH) via a Michael addition reaction. The reaction was stirred at room temperature for 48 hours, resulting in a viscous product. The viscous product was precipitated in an mixture of 400 milliliters of methanol (MeOH) and 250 milliliters of ammonium hydroxide ($NH_4OH$) and subsequently filtered. After soxhlet extraction with methanol (MeOH), 2.25 grams of methyl ester of N-carboxyethyl chitosan (N—CEC) was obtained. N-carboxyethyl chitosan (N—CEC) was obtained by treating the methyl ester with a MeOH-aqueous NaOH solution for 3 hours at 60° C.

Synthesis of N-Propyl Chitosan (N—PC)

N-propyl chitosan (N—PC) was synthesized by the method of Muzzarelli et al, U.S. Pat. No. 4,835,265, incorporated herein by reference. N-propyl chitosan (N—PC) has the following chemical formula:

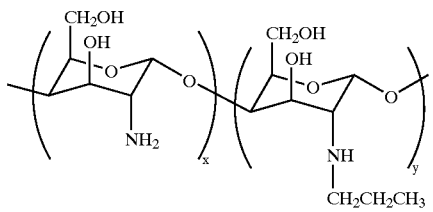

wherein:
x is from about 0.5 to about 0.8;
y is from about 0.2 to about 0.5; and
wherein x and y represent the mole fraction of each unit and the sum of x and y is 1.

Briefly, 2 grams of chitosan dissolved in 1% acetic acid was reacted with 1.36 milliliters of an aqueous solution of propionaldehyde (2 times the molar amount of chitosan).

After 30 minutes, 0.1 molar NaOH was added to the chitosan solution to increase the pH to 4.5, forming a Schiff's base. The Schiff's base was reduced by the addition of 0.5 grams of $NaBH_4$ in 5 milliliters of H2O, and stirring for 12 hours. The pH was susequently adjusted to 10 to precipitate the N-propyl chitosan (N—PC). Soxhlet extraction was performed for 24 hours with ethanol (EtOH), and another 24 hours with diethylether was performed to remove the remaining aldehyde and inorganic products. The percent yield obtained for N-propyl chitosan (N—PC) was 77 percent.

Synthesis of Chitosan-based NONOate Compositions

The chitosan-based diazenium diolates (NONOates) of the present invention were synthesized by reacting nitric oxide gas with the modified chitosan polymers described hereinabove. The above modified chitosan polymers were synthesized so that the primary amine in the chitosan polymer was converted into a secondary amine that serves as the nucleophile reaction site for the binding of the nitric oxide (NO) dimer. Approximately 0.5 grams of the chitosan derivatives, N-carboxybutyl chitosan (N—CBC), N-carboxymethyl chitosan (N—CMC), N-carboxyethyl chitosan (N—CEC), methyl ester of N-carboxyethyl chitosan (N—CEC—Me ester) and N-propyl chitosan (N—PC), were suspended in 40 milliliters of sodium methoxide in methanol solution, and placed in high temperature glass (Ace Glass) bottles equipped with a magnetic stir bar. The solutions were exposed to 100 psi of fresh nitric oxide gas for one hour per day for 7 consecutive days. The resulting products were filtered off. The isolated products were stored in air tight containers at −20° C. in a dessicator. Medium molecular weight chitosan (190,000–300,000) with a deacetylation degree between 75%–85%, levulinic acid, glyoxilic acid, methyl acrylate, propionaldehyde and sodium cyanoborohydride were purchases from Aldrich Chemical Co., and were used without further purification. Nitric oxide gas was purchased from Matheson Gas Products, Inc. All other materials were reagent grade and were purchased from Fisher Scientific, Inc.

Release Profile of Chitosan-based NONOate Compositions

NONOates release NO in aqueous media, and the rate at which NO is released is dependant on the pH and temperature of the media. The release profile for the various chitosan-based NONOate compositions of the present invention was measured using a nitric oxide (NO) analyzer. The nitric oxide analyzer was connected to a 150 milliliter sample chamber consisting of a gas impinger bottle modified with two-way valves that allowed the nitric oxide (NO) gas to accumulate in the sample chamber. The 150 milliliter sample chamber was filled with 25 milliliters of Phosphate Buffered Saline (PBS; pH=7.4), and the solution was degassed for 15 minutes with helium (10 psig at 150 mil/minute). The release profile for each of the chitosan-based NONOate compositions of the present invention was individually determined. Five (5) milligram samples of the chitosan-based NONOate compositions of the present invention were added to the sample chamber, the valves were closed and periodic readings were taken by opening the valves and allowing the nitric oxide released from the chitosan-based NONOate compositions of the present invention to be swept into the detector by way of the helium gas.

Figure 2:
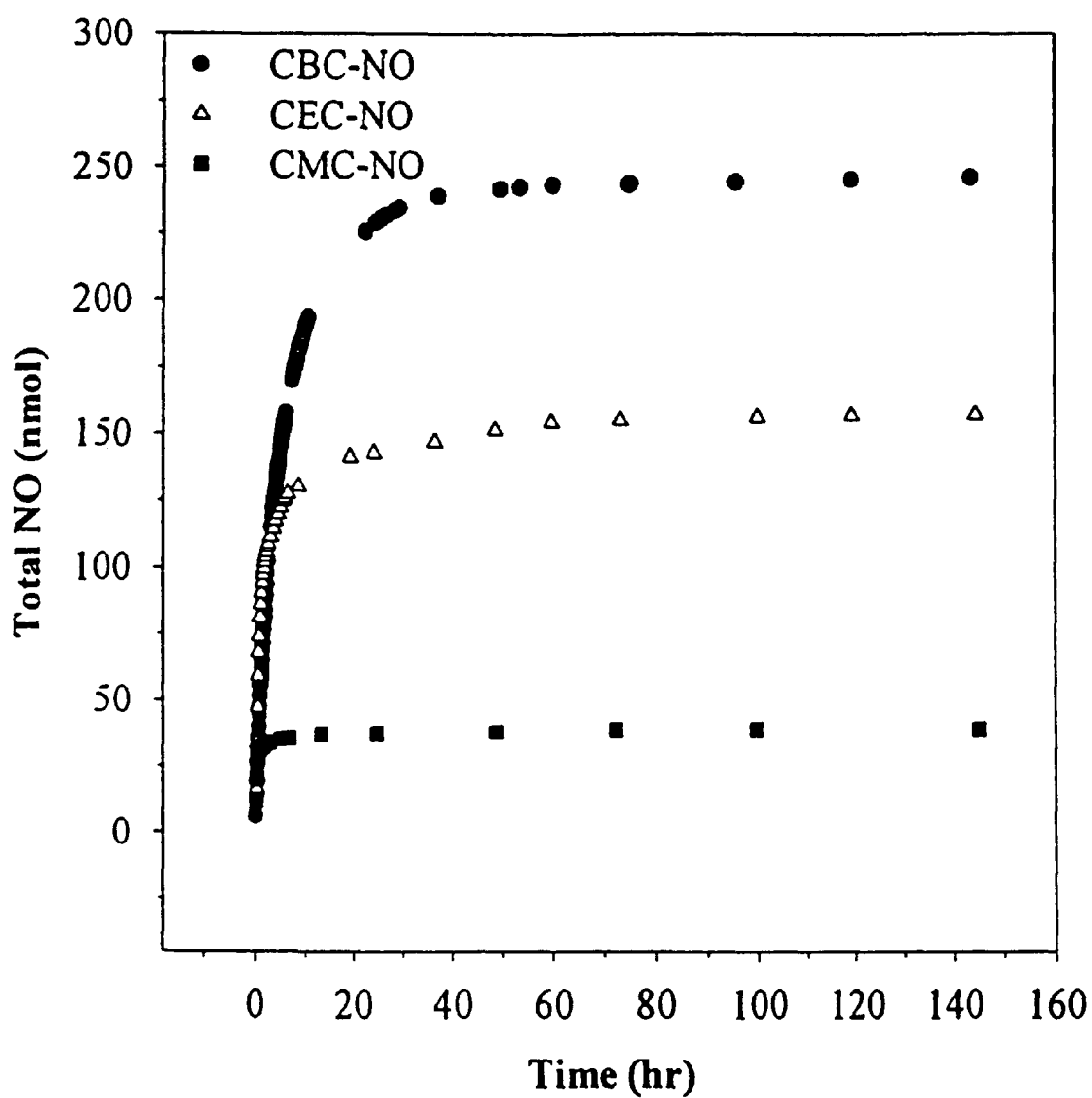
FIG. 2 is a graph comparing the release profile of nitric oxide (NO) from the N-carboxybutyl chitosan NONOate (N—CBC—NO), N-carboxyethyl chitosan NONate (N—CEC—NO) and N-caboxymethyl chitosan NONOate (N—CMC—NO) compositions of the present invention.

The release profiles of nitric oxide (NO) from N-carboxybutyl chitosan NONOate (CBC—NO), N-carboxyethyl chitosan NONOate (CEC—NO) and N-carboxymethyl chitosan NONOate (CMC—NO) are shown in FIG. 2. The release profile data for N-carboxybutyl chitosan NONOate (CBC—NO) contained in FIG. 2, demonstrates that about 250 nanomoles of nitric oxide (NO) is released in an aqueous medium at 37° C. within 40 hours after the N-carboxybutyl chitosan NONOate (CBC—NO) of the present invention was placed in the aqueous medium. The release profile data for N-carboxyethyl chitosan NONOate (CEC—NO) contained in FIG. 2, demonstrates that about 150 nanomoles of nitric oxide (NO) is released in an aqueous medium at 37° C. within 40 hours after adding the N-carboxyethyl chitosan NONOate (CEC—NO) composition of the present invention in the aqueous medium. The release profile data for N-carboxymethyl chitosan NONOate (CMC—NO) contained in FIG. 2, demonstrates that about 35 nanomoles of nitric oxide (NO) is released in an aqueous medium at 37° C. within 40 hours after the N-carboxymethyl chitosan NONOate (CMC—NO) of the present invention added to the aqueous medium.

Figure 3:
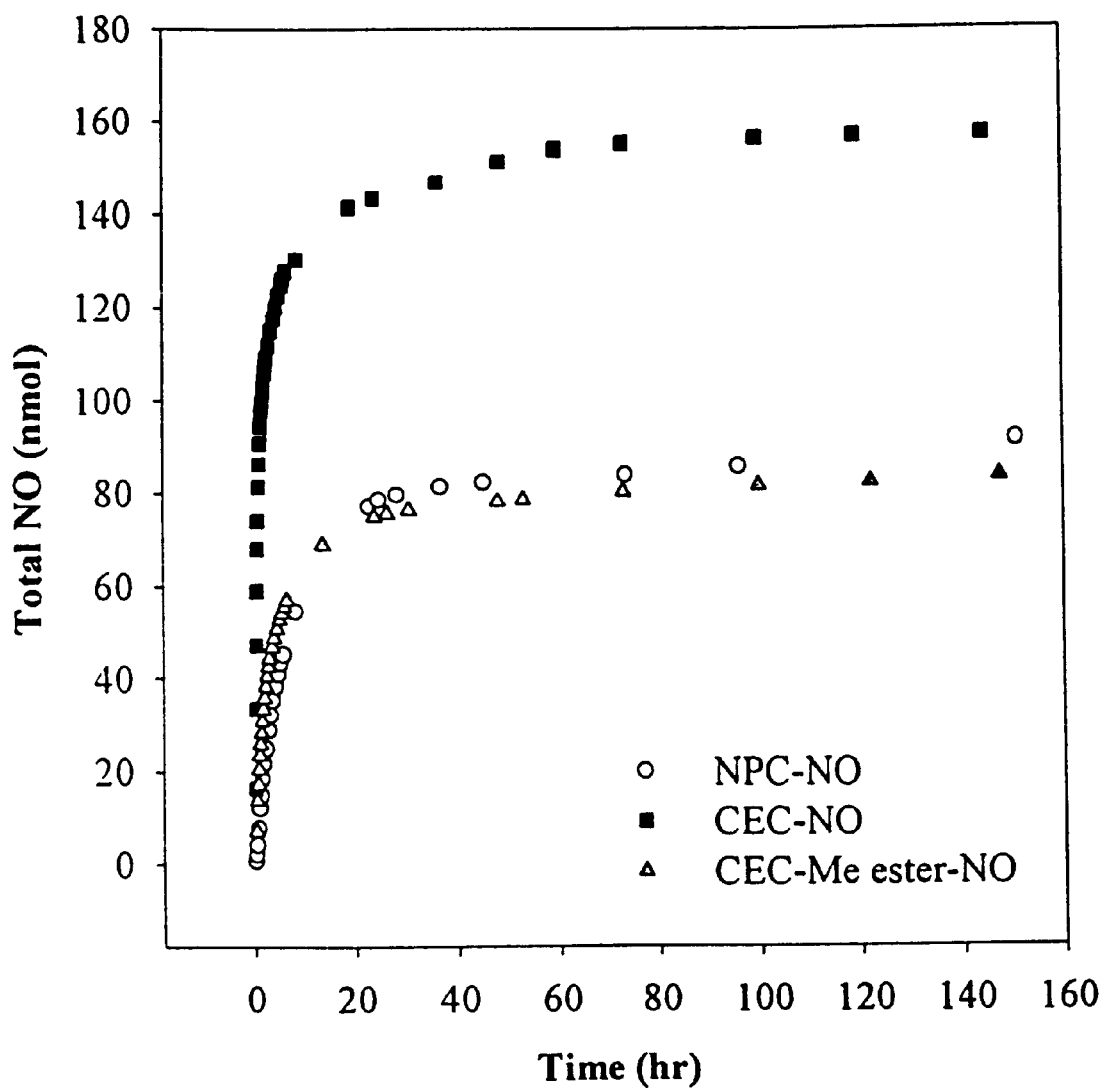
FIG. 3 is a graph comparing the release profile of nitric oxide (NO) from the N-propyl chitosan NONOate (N—PC—NO), N-carboxyethyl chitosan NONate (N—CEC—NO) and N-carboxymethyl chitosan methyl ester NONOate (N—CEC—Me ester-NO) compositions of the present invention.

The release profiles of nitric oxide (NO) from N-propyl chitosan NONOate (N—PC—NO), N-carboxyethyl chitosan NONOate (N—CEC—NO) and the methyl ester of N-carboxyethyl chitosan NONOate (CEC—Me ester—NO) was shown in FIG. 3. The release profile data for N-propyl chitosan NONOate (N—PC—NO) contained in FIG. 3, demonstrates that about 85 nanomoles of nitric oxide (NO) is released into an aqueous medium at 37° C. within 40 hours after adding the N-propyl chitosan NONOate (N—PC—NO) composition of the present invention to the aqueous medium. The release profile data for N-carboxyethyl chitosan NONOate (N—CEC—NO) shown in FIG. 3, again demonstrates that about 150 nanomoles of nitric oxide (NO) is released from N-carboxyethyl chitosan NONOate (N—CEC—NO) in an aqueous medium at 37° C. within 40 hours after adding the N-carboxyethyl chitosan NONOate (N—CEC—NO) of the present invention to the aqueous medium. The release profile data for the methyl ester of N-carboxyethyl chitosan NONOate (CEC—Me-ester-NO) shown in FIG. 3, demonstrates that about 75 nanomoles of nitric oxide (NO) is released from the methyl ester of N-carboxyethyl chitosan NONOate (CEC—Me-ester-NO) of the present invention in an aqueous medium at 37° C. within 40 hours after adding the methyl ester of N-carboxyethyl chitosan NONOate (CEC—Me-ester-NO) to the aqueous medium.

Release kinetic measurements were determined by calculating the concentration of nitric oxide (NO) released from carboxybutyl chitosan NONOate (CBC—NO) with a $KNO_3$ standard curve (100 $\mu$mol/L). A release profile was obtained by plotting the cumulative sum of nitric oxide (NO) produced (nanomoles) versus time (hours). From the graph of the release profile, the concentration of nitric oxide (NO) at infinity was determined. The first order rate was calculated by plotting: $\ln([NO]_\infty - [NO]_t)$ versus time. From this calculation, the k value and the half of carboxybutyl chitosan NONOate (CBC—NO) was determined. The half lives (t½) of chitosan-based NONOate compositions of the present invention are shown in Table I below.

TABLE I

| COMPOUND | HALF LIFE ($T_{1/2}$) OF NO RELEASE |
| --- | --- |
| N-CBC-NO | 244 min. |
| N-CEC-NO | 90 min. |
| N-CEC Me ester-NO | 198 min. |
| N-CMC-NO | 13 min. |
| N-PC-NO | 300 min. |

Thus, it is demonstrated by FIGS. 2 and 3, and Table I above, that the chitosan-based NONOate compositions of the present invention are capable of controlled release of nitric oxide (NO) in aqueous media. It is further demonstrated that the optimal temperature and pH for release of nitric oxide (NO) from the chitosan-based NONOate compositions of the present invention is 37° C. and 7.4, respectively.

The chitosan-based NONOate compositions of the present invention have a wide variety of medical applications in which an effective dosage of nitric oxide is indicated as a preferred treatment. By way of illustration, and not in limitation, the chitosan-based NONOate compositions of the present can be used in the following medical applications for treatment of conditions or disorders in which an effective dosage of nitric oxide is indicated.

It is known that the vascular endothelium produces nitric oxide (NO) which acts as a vasodilator of blood vessels. Many cardiovascular and pulmonary disorders, such as pulmonary hypertension, myocardial ischemia and reperfusion, atherosclerosis and congestive heart failure, are a result of inability of the vascular endothelium to produce physiologically significant levels of nitric oxide (NO). Pulmonary hypertension, for example, results from a block of nitric oxide (NO) synthesis. The chitosan-based NONOate compositions of the present invention can be incorporated into dry powder inhalers, nose drops and aerosol formulations to be administered via inhalation for the site specific delivery and controlled release of nitric oxide (NO) to the pulmonary vasculature; the release nitric oxide (NO) having a vasodilatory effect on the blood vessels, with a corresponding decrease in systolic blood pressure.

It is known that nitric oxide synthesis by macrophages, neutrophils and other inflammatory cells are increased during inflammation and tissue remodeling in normal wounds. It is also known that chitosan derivatives, such as N-carboxybutyl chitosan have significant wound healing and antimicrobial effects. N-carboxybutyl chitosan promotes ordered connective tissue regeneration and decreases in scar formation and wound contraction. The gel forming ability, ease of sterilization and absence of side reaction products of N-carboxybutyl chitosan make it an attractive choice as a wound dressing. Therefore, the chitosan-based NONOate compositions of the present invention has the benefit of nitric oxide (NO) delivery and further medically beneficial properties of the modified chitosan polymer, and may be incorporated into gels, creams and ointments for the topical delivery of nitric oxide (NO) to dermal wounds, especially in patients with compromised macrophage function.

It is also known that endothelium derived nitric oxide (NO) inhibits platelet aggregation and adhesion when platelets come into contact with walls of blood vessels. The chitosan-based NONOate composition of the present invention may be coated onto stents and implants useful for inhibition of platelet aggregation and adhesion to blood vessel walls following medical procedures, such as angioplasty.

Male erection involves neuronally mediated vasorelaxation of the blood vessels of the smooth muscle of the corpora cavernosa. Although the exact mechanism is not fully elucidated, it is known that nitric oxide (NO) mediates male penile erection through relaxation the smooth muscle of the corpora cavernosa. Several in vivo studies have demonstrated that nitric oxide (NO) is the principal neurotransmitter in cavernous smooth muscle. Wang, R., et al., Nitric Oxide mediates penile erection in cats," *The Journal of Urology* 1994, Vol. 151:234–237. Therefore, the chitosan-based NONOate compositions of the present invention may incorporated into topical hydrophilic gels, creams and lubricants, sprays, aerosols, penile implants, dermal patches and condoms, for treatment of penile erection dysfunction in males.

The chitosan-based NONOate compositions of the present invention are useful in any situation when it is desirable to deliver an effective dosage of nitric oxide. Depending on the needs of the particular patient, the chitosan-based NONOate composition of the present invention may be incorporated into dry powder inhalers, aerosols or nose drops to be administered via the nasopharynx. In addition, the chitosan-based NONOate composition of the present invention may be administered by a device inserted into the oropharynx or naseopharynx, or via an endotracheal tube in patients with a tracheostomy.

One skilled in the art will recognized that there various methods of administration of the chitosan-based NONOate composition of the present invention, including, but not limited to, oral administration, inhalation administration, topical administration and parenteral administration. The following methods of administration are provided as illustration, but not of limitation, of the preferred methods of administration of the chitosan-based NONOate composition of the present invention.

The chitosan-based NONOate composition of the present invention can be incorporated into formulations suitable for oral administration. Formulations suitable for oral administration include liquid solutions, tablets, capsules, lozenges, suspensions and emulsions.

The chitosan-based NONOate composition of the present invention can be incorporated into dry powder inhalers, nose drops and aerosol formulations to be administered via inhalation. The aerosol formulations can be placed into acceptable pressurized propellants, such as dichlorofluoromethane, propane, nitrogen, and the like. Although more than one method of administration may be employed, a particular method of administration can be determined based on the specific needs of the patient.

The chitosan-based NONOate composition of the present invention can be incorporated into formulations suitable for parenteral or intravenous administration. Suitable formulations for parenteral or intravenous administration include aqueous and non-aqueous, isotonic, sterile injection solution which may further contain antioxidants, buffers, preservatives, solubilizing agents, chelating agents, stabilizers and thickening agents.

Thus, it is demonstrated that the objects of the present invention are met. The examples included above are for illustrative purposes only and the chitosan-based NONOate composition of the present invention are not limited to them. It is to be understood that the chitosan-based NONOate compositions of the present invention may be incorporated into various delivery systems, and thus, the selection of specific mode of delivery can be determined based on the needs of the patient, without departing from the spirit of the invention herein disclosed and described. Thus, the scope of the invention shall include all modifications and variations that may fall within the scope of the attached claims and equivalent embodiments.

We claim:

1. A nitric oxide donor composition containing a chitosan polymer having nitric oxide ($N_2O_2$—) groups bonded thereto, said composition having the general formula:

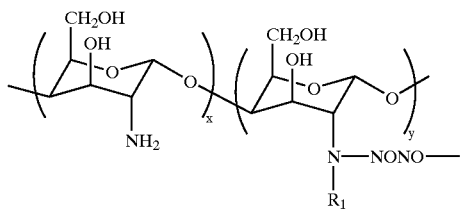

wherein $R_1$ is an organic group having from 5 to about 18 carbon atoms;

wherein x is from about 0.5 to about 0.8;

wherein y is from about 0.2 to about 0.5; and wherein x and y are the mole fractions of each unit and the sum of x and y is 1.

2. The nitric oxide donor composition of claim 1, wherein $R_1$ is selected from N-propyl, N-carboxymethyl, N-carboxyethyl, N-carboxybutyl and the methyl ester of N-carboxyethyl.

3. The nitric oxide donor composition of claim 2, wherein $R_1$ is N-carboxybutyl.

4. The nitric oxide donor composition of claim 1, wherein said nitric oxide donor composition is capable of site specific delivery and controlled release of nitric oxide under physiological conditions.

5. The nitric oxide donor composition of claim 1, wherein said nitric oxide donor composition exhibits first order nitric oxide release kinetics.

6. The nitric oxide donor composition of claim 1, wherein said nitric oxide donor composition contained a nitric oxide carrier molecule possessing medically beneficial properties.

7. The nitric oxide donor composition of claim 1, wherein said nitric oxide donor composition is useful for the treatment of respiratory distress, emphysema, external wounds, internal wounds and coating vascular grafts.

8. A gel comprising the nitric oxide donor composition of claim 1.

9. A cream comprising the nitric oxide donor composition of claim 1.

10. An ointment comprising the nitric oxide donor composition of claim 1.

11. A dermal patch comprising the nitric oxide donor composition of claim 1.

12. A wound dressing comprising the nitric oxide donor composition of claim 1.

13. A medical stent coated with the nitric oxide donor composition of claim 1.

14. An medical implant coated with the nitric oxide donor composition of claim 1.

15. A condom coated with the nitric oxide donor composition of claim 1.

16. A dry powder inhaler comprising the nitric oxide donor composition of claim 1.

17. A nose drop comprising the nitric oxide donor composition of claim 1.

18. An aerosol spray comprising the nitric oxide donor composition of claim 1.

19. A tablet comprising the nitric oxide donor composition of claim 1.

20. A capsule comprising the nitric oxide donor composition of claim 1.

21. A lozenge comprising the nitric oxide donor composition of claim 1.

22. A suspension comprising the nitric oxide donor composition of claim 1.

23. An emulsion comprising the nitric oxide donor composition of claim 1.

24. A parenteral formulation comprising the nitric oxide donor composition of claim 1.

25. A method for preparing a nitric oxide donor composition comprising reacting nitric oxide with a chitosan polymer, said chitosan polymer having the following general formula:

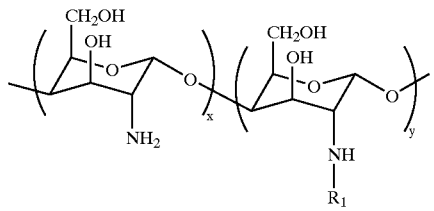

wherein $R_1$ is an organic group having from 5 to about 18 carbon atoms;

wherein x is from about 0.5 to about 0.8;

wherein y is from about 0.2 to about 0.5; and wherein x and y are the mole fractions of each unit and the sum of x and y is 1.

26. The method of claim 25, wherein $R_1$ is selected from N-propyl, N-carboxymethyl, N-carboxyethyl, N-carboxybutyl and the methyl ester of N-carboxyethyl.

27. The method of claim 26, wherein $R_1$ is N-carboxybutyl.

28. The method of claim 25, wherein the method comprises reacting a nitric oxide dimer at a pressure of 80–100 p.s.i. with said chitosan polymer in the presence of sodium methoxide at room temperature.

* * * * *